US008045001B2

(12) United States Patent
Nakao et al.

(10) Patent No.: US 8,045,001 B2
(45) Date of Patent: Oct. 25, 2011

(54) COMPOUND-EYE IMAGING DEVICE

(75) Inventors: Yoshizumi Nakao, Daito (JP); Takashi Toyoda, Daito (JP); Yasuo Masaki, Daito (JP)

(73) Assignee: Funai Electric Co., Ltd., Daito-shi (JP)

( * ) Notice: Subject to any disclaimer, the term of this patent is extended or adjusted under 35 U.S.C. 154(b) by 1337 days.

(21) Appl. No.: 11/645,035

(22) Filed: Dec. 26, 2006

(65) Prior Publication Data
US 2007/0147811 A1 Jun. 28, 2007

(30) Foreign Application Priority Data

Dec. 26, 2005 (JP) ................................. 2005-372832

(51) Int. Cl.
*H04N 21/4415* (2006.01)
(52) U.S. Cl. ............ 348/78; 348/77; 382/118; 382/117; 382/115; 382/128; 382/130; 340/5.82; 340/5.81; 340/5.8; 340/5.53; 340/5.52
(58) Field of Classification Search .................... 348/77, 348/78, 143, 156, 159; 382/115, 117, 118, 382/128, 130; 340/5.8, 5.81, 5.82, 5.2, 5.5, 340/5.51, 5.52, 5.53; 902/3
See application file for complete search history.

(56) References Cited

U.S. PATENT DOCUMENTS
2004/0119851 A1 6/2004 Kaku
2005/0248664 A1* 11/2005 Enge .......................... 348/222.1
2007/0127781 A1* 6/2007 Stewart ......................... 382/110

FOREIGN PATENT DOCUMENTS
| JP | 2003-30647 A | 1/2003 |
| JP | 2003-179807 A | 6/2003 |
| JP | 2004-206688 A | 7/2004 |
| JP | 2004-208279 A | 7/2004 |

OTHER PUBLICATIONS

Emine Krichen et al.; Iris Identification Using Wavelet Packets; Proceedings of the 17th International Conference on Pattern Recognition (ICPR'04); 2004.*

* cited by examiner

*Primary Examiner* — Kenneth R Coulter
(74) *Attorney, Agent, or Firm* — Crowell & Moring LLP

(57) ABSTRACT

A compound-eye imaging device comprises a flash control means for controlling a flash unit to alternatively emit two kinds of near-infrared lights having different wavelengths while multiple single-eye images are read using a rolling shutter; a single-eye image reading means for reading, from the single-eye images, a single-eye image (hereafter "pre-change single-eye image") imaged under a first illumination condition before an illumination condition change by the flash control means, and a single-eye image (hereafter "post-change single-eye image") imaged under a second illumination condition after the illumination condition change; and an eye position detecting means for detecting eye positions in the single-eye images based on a comparison between the read pre-change and post-change single-eye images. This imaging device can further comprise: a face extracting means for extracting a face area based on the detected eye positions; and a personal identification means for performing personal identification based on the extracted face area.

12 Claims, 3 Drawing Sheets

COMPOUND-EYE IMAGING DEVICE

BACKGROUND OF THE INVENTION

1. Field of the Invention

The present invention relates to a compound-eye imaging device, and more particularly to a compound-eye imaging device having a function to detect eye positions of a person from images imaged thereby, the detected eye positions being usable to extract a face area from the images to perform personal identification based on the extracted face area.

2. Description of the Related Art

Imaging devices are known which have a function to recognize a face area contained in an image to perform personal identification. In the field of this kind of devices, Japanese Laid-open Patent Publication 2004-206688 discloses an imaging device to image by intentionally producing a so-called "red-eye" phenomenon, in which eyes of an imaged person are reproduced in red so as to accurately extract a face area. The imaging device. detects the face area based on the red-eye portions in the thus imaged image.

On the other hand, Japanese Laid-open Patent Publication 2003-30647 discloses an imaging device capable of flash imaging. In order to prevent a red-eye phenomenon, the imaging device uses both an image obtained by imaging with flash and an image obtained by imaging without flash so as to detect red-eye areas. This imaging device then electronically corrects the color of the thus detected red-eye areas to normal eye-color.

However, these known imaging devices have problems. In the imaging device disclosed in the above-described Japanese Laid-open Patent Publication 2004-206688, it is required that the red-eye portions in an image be accurately detected so as to accurately extract the face area. The detection of the red-eye portions is described therein as being performed by determining the size and shape of colored areas over the entire area of the image. In order to accurately detect red circular-shaped areas corresponding to the eyes (pupils), this imaging device requires performing a complex process that makes it possible to recognize and determine many patterns.

More specifically, a significantly complex process is required in order to discriminate and recognize red-eye areas of a person present in the image and red circular-shaped areas of e.g. a jewel present in the background of the image. This causes problems such as a significantly long process time until the detection of the red-eye areas, and a significantly high manufacturing cost of the imaging device itself due to the requirement of a significantly large software (program) to perform the complex process. Otherwise, if a simple process is used, there is a risk that the red-eye areas cannot be accurately detected, consequently making it unable to accurately extract a face area from the image, thus making the personal identification impossible.

On the other hand, the imaging device disclosed in the above-described Japanese Laid-open Patent Publication 2003-30647 uses both an image obtained by imaging with flash and an image obtained by imaging without flash so as to detect red-eye areas based on a comparison between both images. Accordingly, this imaging device makes it possible to accurately detect the red-eye areas with a relatively simple process. However, since it requires two steps of imaging with and without flash (two-step imaging), it has a disadvantage in that it takes a long time until the red-eye areas are detected.

SUMMARY OF THE INVENTION

An object of the present invention is to provide a compound-eye imaging device having a function to accurately detect, from images imaged thereby, eye positions of a person with a relatively simple processing program in a relatively short time, making it possible to use the detected eye positions for extracting a face area and to perform accurate personal identification based on the extracted face area in a relatively short time.

According to the present invention, this object is achieved by a compound-eye imaging device comprising: multiple optical lenses arranged in an array; a solid state imaging element for imaging multiple single-eye images formed by the multiple optical lenses, respectively; a shutter means for sequentially reading, with a time difference, the multiple single-eye images formed on the solid state imaging element; a storage means for storing the multiple single-eye images read using the shutter means; a flash unit for emitting flash light to illuminate a target object to be imaged; a flash control means for changing the wavelength, presence/absence or intensity of the flash light emitted from the flash unit while the multiple single-eye images are read using the shutter means; a single-eye image reading means for reading, from the multiple single-eye images stored in the storage means, a single-eye image imaged under a first illumination condition before the flash control means changes an illumination condition (such single-eye image hereafter referred to as pre-change single-eye image), and a single-eye image imaged under a second illumination condition different from the first illumination condition after the flash control means changes the illumination condition (such single-eye image hereafter referred to as post-change single-eye image); and an eye position detecting means for detecting eye positions in the single-eye images based on a comparison between the pre-change and post-change single-eye images read by the single-eye image reading means.

This compound-eye imaging device can detect eye positions accurately and in a short time, even using a relatively simple processing program for the eye position detection. This compound-eye imaging device can be used to enable accurate personal identification in a relatively short time.

Preferably, the eye position detecting means detects the eye positions in the single-eye images based on a difference between the pre-change and post-change single-eye images.

Further preferably, the shutter means includes a rolling shutter.

Still further preferably, the flash control means controls the flash unit to alternatively emit two kinds of near-infrared lights having different wavelengths while multiple single-eye images are read using the shutter means. This can increase the difference in color (brightness) between the eye areas in the pre-change and post-change single-eye images, so that the eye positions can be detected with improved accuracy.

The compound-eye imaging device can further comprise: a face extracting means for extracting a face area in the single-eye images based on the eye positions detected by the eye position detecting means in the single-eye images; and a personal identification means for performing personal identification based on the face area extracted by the face extracting means. This compound-eye imaging device enables accurate personal identification in a relatively short time.

While the novel features of the present invention are set forth in the appended claims, the present invention will be better understood from the following detailed description taken in conjunction with the drawings.

BRIEF DESCRIPTION OF THE DRAWINGS

The present invention will be described hereinafter with reference to the annexed drawings. It is to be noted that all the drawings are shown for the purpose of illustrating the technical concept of the present invention or embodiments thereof, wherein.

DESCRIPTION OF THE PREFERRED EMBODIMENTS

Figure 1:
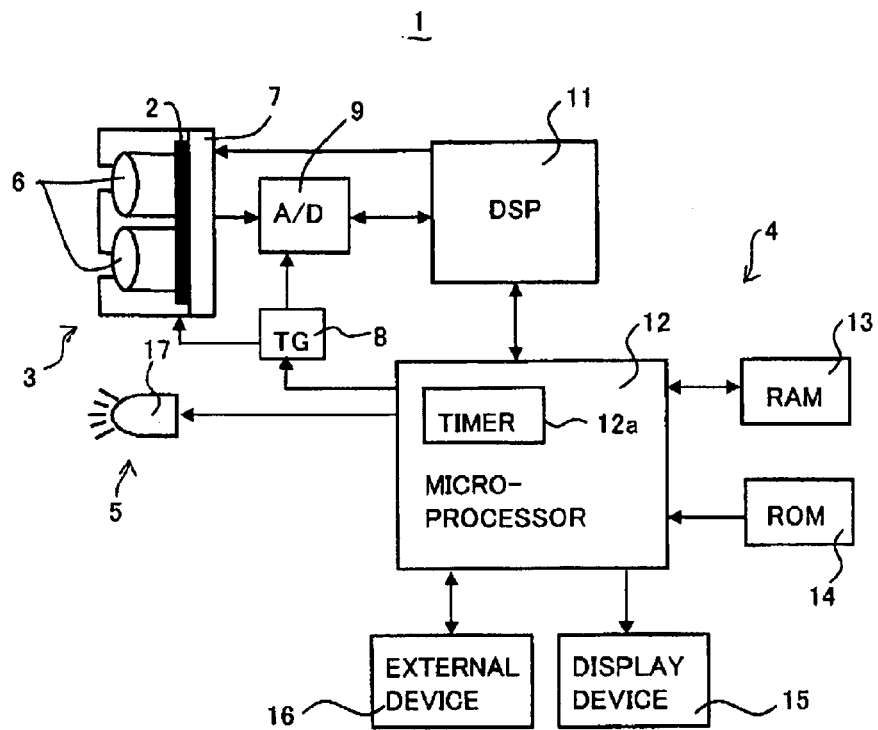
FIG. 1 is a schematic block diagram of a compound-eye imaging device according to an embodiment of the present invention.

Embodiments of the invention, as best mode for carrying out the invention, will be described hereinafter with reference to the drawings. It is to be understood that the embodiments herein are not intended as limiting, or encompassing the entire scope of, the invention. Note that like parts are designated by like reference numerals or characters throughout the drawings.

FIG. 1 is a schematic block diagram of a compound-eye imaging device 1 according to an embodiment of the present invention. The compound-eye imaging device 1 comprises: an optical system section 3 for collecting light from a target object (person) to be imaged to form multiple single-eye images on a solid state imaging element 2; a circuit section 4 for electronically processing the single-eye images imaged by the solid state imaging element 2 to perform personal identification; and a flash unit 5 connected to, and driven or turned on by, the circuit section 4 to emit flash light at a timing described later for illuminating the target object to be imaged. In the present specification, the term "single-eye" is used to mean an optical system using e.g. a microlens, and the term "compound-eye" is used to mean an optical system using e.g. multiple microlenses, so that a "single-eye image" is an image formed e.g. by a microlens, and a "compound-eye image" is an image formed e.g. by synthesizing or combining the "single-eye images".

Figure 2:
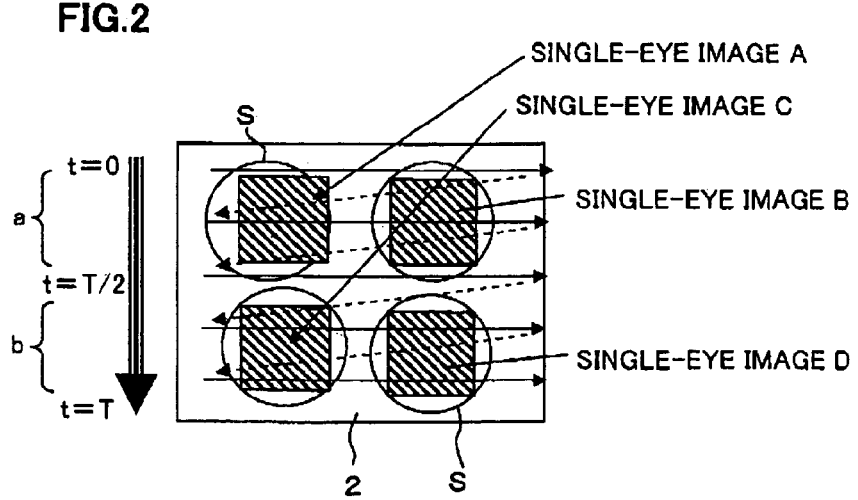
FIG. 2 is a schematic view showing a solid state imaging element in the compound-eye imaging device, and an arrangement of four single-eye images formed thereon.

The optical system section 3 comprises: four optical lenses 6 (two lenses 6 shown) arranged in an array of two rows and two columns and having mutually parallel optical axes; and a solid state imaging element 2 for imaging four images (single-eye images) respectively formed by the optical lenses 6. The solid state imaging element 2 is formed of a semiconductor substrate 7, and is e.g. a CMOS (Complementary Metal Oxide Semiconductor) image sensor. As shown in FIG. 2, which is a schematic view showing the solid state imaging element 2 in the compound-eye imaging device 1, and an arrangement of the four single-eye images formed thereon, the four single-eye images as designated by A, B, C and D are formed on the solid state imaging element 2 in two rows and two columns.

Referring to FIG. 1 and FIG. 2, the respective optical lenses 6 collect and condense light onto the solid state imaging element 2 to form images S thereon which are respectively shown by circles. Square-shaped single-eye images A, B, C and D are extracted from the respective images S. The respective single-eye images A, B, C and D are converted by the solid state imaging element 2 into analog signals, and sequentially read with a time difference at a predetermined timing (i.e. predetermined read timing) which is generated by a timing generator 8 described later.

More specifically, as shown in FIG. 2, the single-eye images are sequentially read in order from single-eye image A to single-eye image B, single-eye image C and single-eye image D. In the present embodiment, the combination of the solid state imaging element 2 and the timing generator 8 to sequentially read the single-eye images A, B, C and D with a time difference at the predetermined sequential read timing forms a rolling shutter (claimed "shutter means"). The single-eye images A, B, C and D are formed (by exposure) on the solid state imaging element 2 at a timing the same as the sequential read timing. This will be described in detail below.

The first two single-eye images A and B are read while the flash unit 5 is turned on to emit flash light during the time between t=0 and t=T/2, and the next two other single-eye images C and D are read while the flash unit 5 does not emit flash light during the time between t=T/2 and t=T as will also be described with reference to FIG. 3. In order to read the first two single-eye images A and B, first of all, the first line (t=0) for the images S corresponding to the single-eye images A and B is read from left to right in FIG. 2, and then the second line is read similarly. In this way, the lines are sequentially read till the last line (t=T/2). Thus, the two single-eye images A and B are read with a slight time difference (time delay) therebetween.

In order to read the next two single-eye images C and D, the first line (t=T/2) for the images S corresponding to the single-eye images C and D is read from left to right in FIG. 2, and then the second line is read similarly. In this way, the lines are sequentially read till the last line (t=T). Thus, the two single-eye images C and D are read with a slight time difference therebetween, and with a time difference (time delay) of T/2 from the two single-eye images A and B. Note that although three lines with arrow heads pointing right are drawn for the single-eye images A and B, and two lines for the single-eye images C and D, they only schematically show the concept of the direction and sequence of the reading.

Referring back to FIG. 1, the circuit section 4 will be described. The circuit section 4 comprises: an A/D (Analog to Digital) converter 9 for converting analog signals from the solid state imaging element 2 to digital signals; a DSP (Digital Signal Processor) 11 for capturing the digital signals from the A/D converter 9; and a timing generator 8 connected to the solid state imaging element 2 and the A/D converter 9 for controlling the timing of reading the single-eye images, as analog signals, from the solid state imaging element 2, and for controlling the timing of converting the analog signals to digital signals.

The circuit section 4 further comprises: a microprocessor 12 (claimed "flash control means", "single-eye image reading means", "eye position detecting means", "face extracting means", and "personal identification means") connected to the DSP 11 for processing, according to a process described later, the single-eye images captured by the DSP 11; and a RAM (Random Access Memory) 13 (claimed "storage means"), a ROM (Read Only Memory) 14 and a display device 15 such as a liquid crystal panel which are connected to the microprocessor 12. The RAM 13 temporarily stores multiple single-eye images read from the solid state imaging element 2, while the ROM 14 stores pre-registered face images and a processing program for performing personal identification as described later. The microprocessor 12 has a timer 12a having a predetermined time-out period to count time so as to determine elapse of the time-out period in a personal identification process described later. An external device 16 such as a personal computer is connected to the microprocessor 12 if desired by a user.

The flash unit 5 has an LED 17 as a light source which, under the control of the microprocessor 12, emits a near-infrared light having a wavelength of 850 nm in synchronization with the read timing for the microprocessor 12 to read the single-eye images from the solid state imaging element 2. More specifically, the microprocessor 12 activates the timing generator 8, and then drives or turns on the flash unit 5 to emit flash light with a predetermined light intensity P in a first half period "a" (between t=0 and t=T/2) in which the single-eye images A and B are read from the solid state imaging element 2, and to stop emitting flash light in a second half period "b" (between t=T/2 and t=T), as shown in FIG. 2 and FIG. 3.

Figure 3:
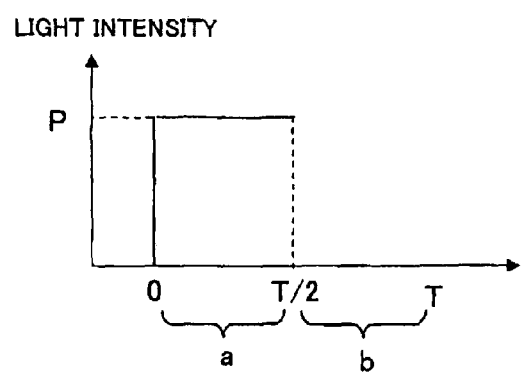
FIG. 3 is a graph showing a control timing of a flash unit in the compound-eye imaging device.

FIG. 3 is a graph showing a control timing of the flash unit 5 in the compound-eye imaging device 1. The read period ("a"+"b") corresponds to the total read period for reading all the single-eye images A, B, C and D (in the two rows and two columns) on the solid state imaging element 2, so that the first half period "a" corresponds to the read period for reading the single-eye images A and B in the upper row, while the second half period "b" corresponds to the read period for reading the single-eye images C and D in the lower row, as shown schematically in FIG. 2.

Figure 4:
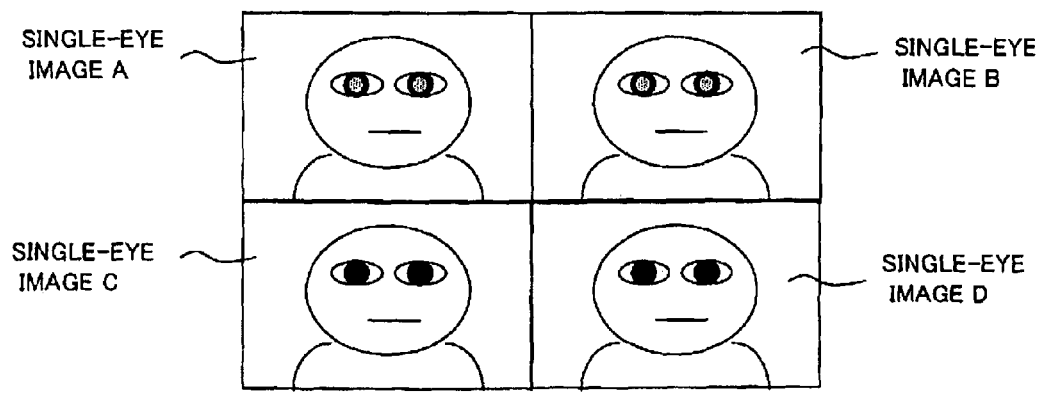
FIG. 4 is a schematic view showing an example of a set of single-eye images imaged by the compound-eye imaging device.

Thus, the single-eye images A and B, which are read in the first half period "a" of the total read period, are images (pre-change single-eye images) obtained by imaging a target object illuminated by the flash unit 5. On the other hand, the single-eye images C and D, which are read in the second half period "b" of the total read period, are images (post-change single-eye images) obtained by imaging the target object which is not illuminated by the flash unit 5. This is specifically shown in FIG. 4, which is a schematic view showing an example of a set of single-eye images imaged by the compound-eye imaging device 1. Referring to FIG. 4, the single-eye images A and B are those in which the red-eye phenomenon occurs because the target object is illuminated by the flash unit 5, while the single-eye images C and D are those in which the red-eye phenomenon does not occur because the target object is not illuminated by the flash unit 5.

The red-eye phenomenon is used in the present embodiment for the eye position detection and the personal identification. Here, the flash unit 5 uses LED 17, which emits a near-infrared light having a wavelength of 850 nm, as a light source of the flash unit 5. Accordingly, the color of the pupils in the reproduced single-eye images A and B is bright red due to the light reflected from the retinas of the target object (person) illuminated by the flash unit 5, whereas the other areas including the flesh areas in the reproduced single-eye images A and B are substantially natural-colored, i.e. not excessively bright. Thus, as compared with the case of using normal visible light as a light source of the flash unit, the use of the near-infrared light as a light source of the flash unit 5 improves the accuracy in the eye position detection (used in a personal identification process described later) based on a comparison between the pre-change single-eye images and the post-change single-eye images. The reason is as follows.

The eye positions are detected by comparing the pre-change single-eye images A and B with the post-change single-eye images C and D. If a near-infrared light is used (using LED 17 to emit a near-infrared light having a wavelength of 850 nm as a light source of the flash unit 5), a significant difference in brightness between the pre-change and post-change single-eye images is produced in the eye areas (more specifically, pupils as reflected from the retinas), whereas no significant difference in brightness is produced in the other areas between the pre-change and post-change single-eye images. That is, a difference signal produced by the comparison (i.e. subtraction) between the pre-change and post-change single-eye images is produced by the difference in brightness in the eye areas, so that the eye positions can be accurately detected by using the difference signal between the pre-change and post-change single-eye images.

In contrast, if ordinary visible light is used as a light source of the flash unit 5, not only the color of the pupils in the reproduced single-eye images A and B (pre-change single-eye images) as reflected from the retinas of the target object (person) is bright, but the color of the other areas (non-eye areas) including the flesh areas therein is also bright (high brightness). Accordingly, significant differences in brightness between the pre-change single-eye images and post-change single-eye images (which are not illuminated by the flash unit 5) are produced not only in the eye areas, but also in the other areas. In other words, a difference signal generated by the comparison between the pre-change and post-change single-eye images is generated by the difference in brightness, not only in the eye areas, but also in the other areas, so that it is difficult to accurately detect the eye positions by simply using the difference signal between the pre-change and post-change single-eye images. This is the reason why the use of the near-infrared light improves the accuracy in detecting the eye positions.

The mode of changing the flash from the first half period "a" to the second half period "b" can be modified to improve the accuracy in detecting the eye positions by further reducing the difference in brightness of the non-eye areas between the pre-change and post-change single-eye images while maintaining a sufficient difference in brightness of the eye areas between the pre-change and post-change single-eye images. One modified mode is to allow the flash unit 5 to emit flash light with a light intensity P in the first half period "a" of the read period, and with a light intensity P/2 (or other predetermined light intensity lower than P) in the second half period "b". This is to reduce the difference in intensity of the flash light from the flash unit 5 between the first half period "a" and the second half period "b" of the read period while maintaining a sufficient difference in the brightness of the eye areas in the reproduced single-eye images between the pre-change and post-change single-eye images.

Another modified mode is to allow the flash unit 5 to have two LEDs for emitting near-infrared lights having wavelengths of 850 nm and 940 nm, respectively, so as to emit a near-infrared light having the wavelength of 850 nm in the first half period "a" of the read period, and a near-infrared light having the wavelength of 940 nm in the second half period "b". That is, the microprocessor 12 or flash control means controls the flash unit 5 to alternatively emit two kinds of near-infrared lights having different wavelengths while multiple single-eye images are read using the shutter means. This makes it possible to minimize the difference in brightness of the non-eye areas, while maintaining a sufficient difference in brightness of the eye areas, in the reproduced single-eye images between the pre-change and post-change single-eye images. This further improves the accuracy in detecting the eye positions.

As apparent from the descriptions here, the microprocessor 12 or flash control means in the compound-eye imaging device 1 serves to change illumination conditions by changing (a) the wavelength of the flash light, (b) the presence/absence of the flash light, or (c) the intensity of the flash light emitted from the flash unit 5 while the single-eye images are read using the microprocessor 12 or shutter means. That is, the microprocessor 12 and the flash unit 5 provide a first illumination condition before the microprocessor 12 or flash control means changes an illumination condition in imaging pre-change single-eye images, and also provide a second illumination condition different from the first illumination condition after the microprocessor 12 or flash control means changes the illumination condition for post-change single-eye images, while the microprocessor 12 or single-eye image reading means read the multiple single-eye images.

Hereinafter, referring to the flow chart of FIG. 5, a personal identification process including an eye position detection process as performed by the compound-eye imaging device 1 according to the present embodiment will be described. Normal imaging is performed while the microprocessor 12 does not turn on the flash unit 5, so that the flash unit 5 does not emit flash light (S1). Then, the microprocessor 12 determines whether there is a movement of a target object (person) in single-eye images obtained or imaged by the normal imaging (namely the microprocessor 12 performs motion detection to determine whether the target objects changes in position among the single-eye images) (S2). If the microprocessor 12 determines that there is no movement of the target object (NO in S2), the microprocessor 12 continues the normal imaging.

On the other hand, if the microprocessor 12 determines that there is a movement of the target object (YES in S2), the microprocessor 12 allows the timer 12a therein having a predetermined time-out period to start counting time, and controls the flash unit 5 in a manner described above with reference to FIG. 2 and FIG. 3 (S3) (the microprocessor 12 thus serving as claimed "flash control means") so as to read single-eye images A, B, C and D in this order, and temporarily stores these images in the RAM 13 (S4). Note here that the function of the motion detection by the microprocessor 12 in step S2 can be replaced by a manual operation using a start button (not shown) which, when pressed by a user, allows the flow chart to go to step S3 (flash control) from step S1 (normal imaging).

Thereafter, the microprocessor 12 reads one pre-change single-eye image (e.g. single-eye image A) and one post-change single-eye image (e.g. single-eye image C) from the single-eye images A, B, C and D stored in the RAM 13 (the microprocessor 12 thus serving as claimed "single-eye image reading means"), and determines whether there is a difference between the pre-change and post-change single-eye images (S5). More specifically, the microprocessor 12 produces a differential image between the single-eye images A and C, and determines whether the differential image contains a portion having a differential value larger than a predetermined threshold value. Hereafter, a differential value larger than the predetermined threshold value will be referred to as "significant differential value". For example, if, as shown in FIG. 4, the eye areas (pupil areas) in the reproduced single-eye image A are red ("red-eye" phenomenon), while the eye areas (pupil areas) in the reproduced single-eye image C are natural-colored (e.g. black), the microprocessor 12 determines that the differential image has a significant differential value in the eye areas.

If the microprocessor 12 determines that the differential image contains no significant differential value (NO in S5), the microprocessor 12 determines whether the predetermined time-out period has elapsed (namely, whether the time period, from the time the microprocessor 12 has determined YES in S2, has exceeded the predetermined time-out period) (S6). If the microprocessor 12 determines that the time-out period has elapsed (YES in S6), the process returns to step S1 (normal imaging). On the other hand, if the microprocessor 12 determines that the time-out period has not elapsed (NO in S6), the process returns to step S3 to repeat steps S3 to S5 as shown by the two circled A in FIG. 5 until determining YES in step S5 or YES in steps S6. Based on this timer control, the microprocessor 12 repeats imaging images for eye position detection for ultimate personal identification using the flash unit 5 in a predetermined time.

Here, it is also possible to design the compound-eye imaging device 1 so that if the microprocessor 12 detects no significant difference or differential value (in eye areas) in the differential image between the pre-change and post-change single-eye images even by repeating imaging images for eye detection (for personal identification) in the predetermined time, a message to that effect is displayed on the display device 15 or the external device 16. Note that in step S5 where the microprocessor 12 reads one pre-change single-eye image (e.g. single-eye image A) and one post-change single-eye image (e.g. single-eye image C) from the single-eye images A, B, C and D stored in the RAM 13, it is possible to predetermine the single-eye images to be read. It is also possible to design the compound-eye imaging device 1 so that all the pre-change single-eye images (single-eye images A and B) and the post-change single-eye images (single-eye images C and D) are read, and that single-eye images having less noises (clearer single-eye images) are selected for use from the respective pre-change and post-change single-eye images.

The determination by the microprocessor 12 in step 5 to determine whether or not there is a significant difference or differential value between the two (pre-change and post-change) single-eye images is made simply by producing a differential image between the two images, and by determining whether the differential image contains a portion (eye areas) having a differential value larger than a predetermined threshold value as described above. Accordingly, such determination in step S5 can be made with a relatively simple processing program in a short time. Furthermore, in the present embodiment, the microprocessor 12 controls the flash unit 5 in a manner described above with reference to FIG. 2 and FIG. 3 so as to increase the difference in color (brightness) between the eye areas in the pre-change and post-change single-eye images as described above, so that the eye positions can be detected with improved accuracy.

Figure 5:
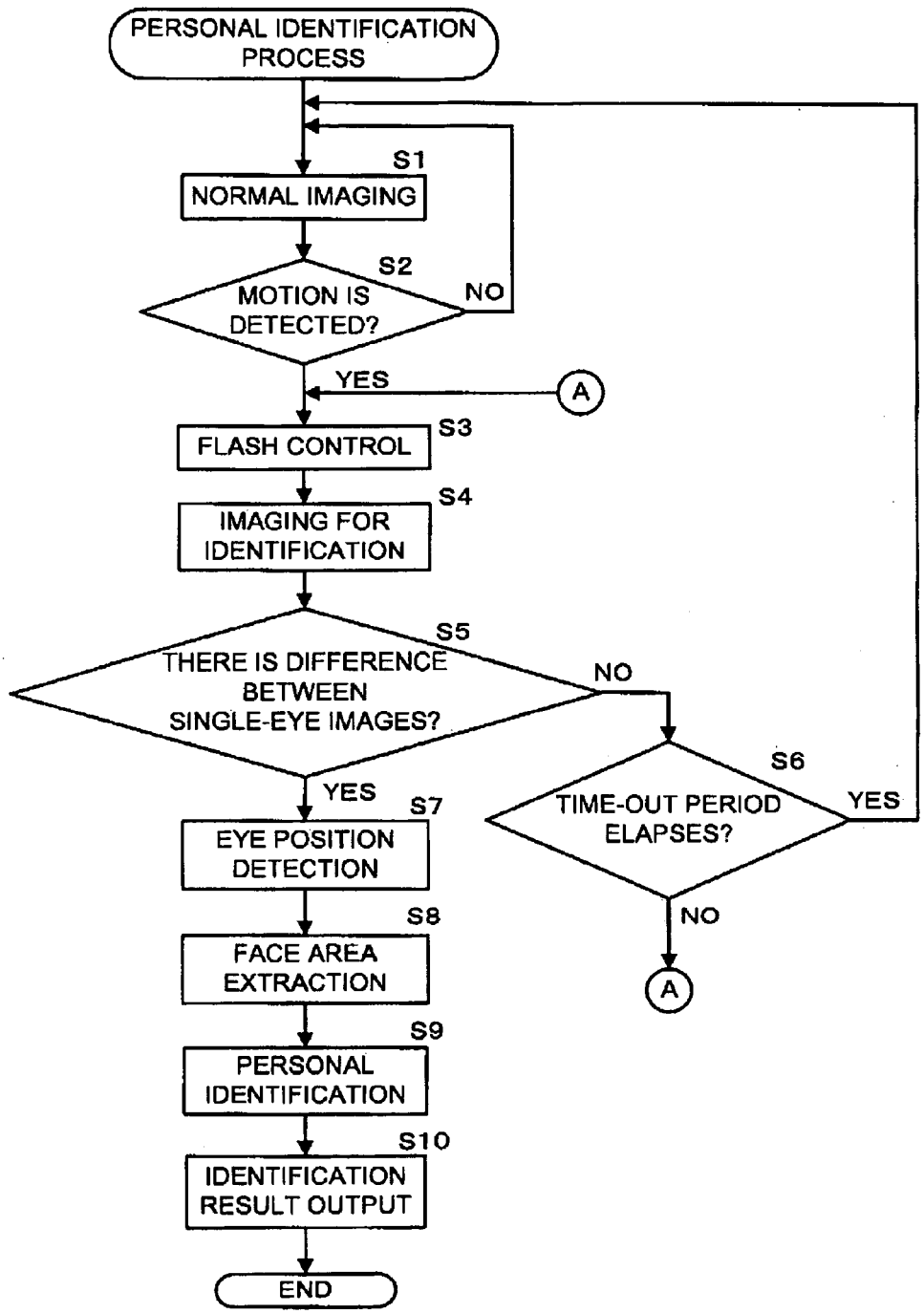
FIG. 5 is a flow chart showing a personal identification process including an eye position detection process as performed by the compound-eye imaging device.

Referring back to step S5 in the flow chart of FIG. 5, when the microprocessor 12 determines that there is a significant difference or differential value between the pre-change and post-change single-eye images (YES in S5), the microprocessor 12 detects positions of the differential portions (eye areas), i.e. performs eye position detection (S7) (the microprocessor thus serving as claimed "eye position detecting means"). Based on the detected positions of the differential portions (eye areas), the microprocessor 12 extracts a face area (S8) (the microprocessor 12 thus serving as claimed "face extracting means"). This extraction of the eye area is done by recognizing a flesh color area around the detected differential portions (eye areas). This process of extracting the face area is performed in the post-change single-eye image (single-eye image C) as imaged without the flash light of the flash unit 5, because the color of the face area in the reproduced single-eye image is preferably closer to natural color. Since the positions of the eye areas are accurately detected, the face area extraction can also be accurately done using a relatively simple processing program.

Next, the microprocessor 12 compares an image of the thus extracted face area with images of face areas pre-registered in and read from the ROM 14 so as to perform personal identification (S9) (the microprocessor 12 thus serving as claimed "personal identification means"). Thereafter, the microprocessor 12 outputs, to the display device 15 or the external device 16, a message indicating the result of the personal identification (S10). Various known technologies can be used as technologies to extract the face area in step S8, and compare the image of the extracted face area with pre-registered images of face areas so as to perform personal identification in step S9.

As described in the foregoing, the compound-eye imaging device 1 according to the present embodiment detects eye positions based on a comparison between pre-change and post-change single-eye images. Accordingly, the eye-positions can be detected accurately and in a short time, using a relatively simple processing program for the eye position detection, thereby enabling accurate personal identification. In addition, in contrast to conventional devices such as described in Japanese Laid-open Patent Publication 2003-30647, the compound-eye imaging device 1 does not require two-step imaging, but uses one-step imaging to make it possible to obtain single-eye images under different (changed) illumination conditions (for example, with and without flash, or with different light wavelengths). This can also reduce the time required to perform personal identification.

It is to be noted that the present invention is not limited to the above-described embodiment, and various modifications are possible. For example, in the present embodiment, the optical lenses 6 arranged in an array as well as single-eye images formed by the optical lenses 6 on the solid state imaging element 2 are in a matrix of two rows and two columns. However, this can be in a modified arrangement such as a matrix of three rows and three columns. A simplest example of the modified arrangement is two optical lenses 6 arranged vertically, namely in two rows and one column. In this case, one pre-change single-eye image and one post-change single-eye image are formed by the two optical lenses. In addition, although 850 nm and 940 nm are exemplified above as the wavelengths of the near-infrared lights to be emitted from the flash unit 5 (LED or LEDs), they are not required to be exactly 850 nm and 940 nm, and can be other wavelengths near 850 nm and 940 nm.

The present invention has been described above using presently preferred embodiments, but such description should not be interpreted as limiting the present invention. Various modifications will become obvious, evident or apparent to those ordinarily skilled in the art, who have read the description. Accordingly, the appended claims should be interpreted to cover all modifications and alterations which fall within the spirit and scope of the present invention.

This application is based on Japanese patent application 2005-372832 filed Dec. 26, 2005, the content of which is hereby incorporated by reference.

What is claimed is:

1. A compound-eye imaging device comprising:
    multiple optical lenses arranged in an array;
    a solid state imaging element for imaging multiple single-eye images formed by the multiple optical lenses, respectively;
    a shutter means for sequentially reading, with a time difference, the multiple single-eye images formed on the solid state imaging element;
    a storage means for storing the multiple single-eye images read using the shutter means;
    a flash unit for emitting flash light to illuminate a target object to be imaged;
    a flash control means for changing the wavelength, presence/absence or intensity of the flash light emitted from the flash unit while the multiple single-eye images are read using the shutter means;
    a single-eye image reading means for reading, from the multiple single-eye images stored in the storage means, a single-eye image imaged under a first illumination condition before the flash control means changes an illumination condition (such single-eye image hereafter referred to as pre-change single-eye image), and a single-eye image imaged under a second illumination condition different from the first illumination condition after the flash control means changes the illumination condition (such single-eye image hereafter referred to as post-change single-eye image); and
    an eye position detecting means for detecting eye positions in the single-eye images based on a comparison between the pre-change and post-change single-eye images read by the single-eye image reading means.

2. The compound-eye imaging device according to claim 1, wherein the eye position detecting means detects the eye positions in the single-eye images based on a difference between the pre-change and post-change single-eye images.

3. The compound-eye imaging device according to claim 2, wherein the shutter means includes a rolling shutter.

4. The compound-eye imaging device according to claim 3, wherein the flash control means controls the flash unit to alternatively emit two kinds of near-infrared lights having different wavelengths while multiple single-eye images are read using the shutter means.

5. The compound-eye imaging device according to claim 2, wherein the flash control means controls the flash unit to alternatively emit two kinds of near-infrared lights having different wavelengths while multiple single-eye images are read using the shutter means.

6. The compound-eye imaging device according to claim 1, wherein the shutter means includes a rolling shutter.

7. The compound-eye imaging device according to claim 1, which further comprises:
    a face extracting means for extracting a face area in the single-eye images based on the eye positions detected by the eye position detecting means in the single-eye images; and
    a personal identification means for performing personal identification based on the face area extracted by the face extracting means.

8. The compound-eye imaging device according to claim 7, wherein the eye position detecting means detects the eye positions in the single-eye images based on a difference between the pre-change and post-change single-eye images.

9. The compound-eye imaging device according to claim 8, wherein the shutter means includes a rolling shutter.

10. The compound-eye imaging device according to claim 9, wherein the flash control means controls the flash unit to alternatively emit two kinds of near-infrared lights having different wavelengths while multiple single-eye images are read using the shutter means.

11. The compound-eye imaging device according to claim 8, wherein the flash control means controls the flash unit to alternatively emit two kinds of near-infrared lights having different wavelengths while multiple single-eye images are read using the shutter means.

12. The compound-eye imaging device according to claim 7, wherein the shutter means includes a rolling shutter.

* * * * *